(12) United States Patent
Yonehara et al.

(10) Patent No.: US 7,425,519 B2
(45) Date of Patent: Sep. 16, 2008

(54) LIQUID PHASE OXYGENATION REACTION USING TUNGSTEN SPECIES

(75) Inventors: Koji Yonehara, Kyoto (JP); Yasutaka Sumida, Neyagawa (JP); Kazuhisa Hirata, Tsukuba (JP)

(73) Assignee: Nippon Shokubai Co., Ltd., Osaka-Shi (JP)

( * ) Notice: Subject to any disclaimer, the term of this patent is extended or adjusted under 35 U.S.C. 154(b) by 699 days.

(21) Appl. No.: 10/621,399

(22) Filed: Jul. 18, 2003

(65) Prior Publication Data

US 2004/0127754 A1 Jul. 1, 2004

(30) Foreign Application Priority Data

Jul. 18, 2002 (JP) ............................. 2002-209987

(51) Int. Cl.
- C07C 27/00 (2006.01)
- C07C 41/00 (2006.01)
- B01J 31/00 (2006.01)
- C07D 305/00 (2006.01)

(52) U.S. Cl. .................. 502/150; 568/954; 568/959; 549/263

(58) Field of Classification Search ............ 568/954, 568/959; 502/150; 549/263
See application file for complete search history.

(56) References Cited

U.S. PATENT DOCUMENTS

| 2,870,171 A | 1/1959 | Gable |
| 3,627,701 A | 12/1971 | Coyne et al. |
| 5,430,161 A | 7/1995 | Brown et al. |
| 6,229,028 B1 | 5/2001 | Neumann et al. |

FOREIGN PATENT DOCUMENTS

| CN | 1260786 A | 7/2000 |
| EP | 0109273 A1 | 5/1984 |
| EP | 0 930 308 A1 | 7/1999 |
| GB | 2 309 655 A | 8/1997 |
| WO | WO-93/00338 | 1/1993 |
| WO | WO 94/21583 | 9/1994 |
| WO | WO-98/54165 A1 | 12/1998 |
| WO | WO 99/62894 | 12/1999 |

OTHER PUBLICATIONS

T. Yamaguchi, et al. "Isomerization and Disproportionation of Olefins over Tungsen Oxides Supported on Various Oxides", Journal of Catalysis 65, 442-447 (1980).

L. L. Murrell, et al., "Supported Transition Metal Oxides as Acid Cracking Catalysts: Periodic Trends and Their Relationship to Activity an Selectivity", Journal of Catalysis 107, 463-470 (1987).

Ostromecki et al., "The Influence of metal oxide additives on the molecular structures of a surface tungsten oxide species on alumina: I. Ambient conditions", Journal of Molecular Catalysis A: Chemical 132 (1998) p. 43-57.

E. Briot et al., "Aqueous acidic hydrogen peroxide as an efficient medium for tungsten insertion into MCM-41 mesoporous molecular sieves with high metal dispersion", Journal of Materials Chemistry, 2000, 10, p. 953-958.

T. Sakamoto et al., "Selective epoxidation of olefins by hydrogen peroxide in water using a polyoxometalate catalyst supported on chemically modified hydrophobic mesoporous silica gel", Tetrahedron Letters 41 (2000) p. 10009-10012.

Y. Watanabe et al., "Epoxidation of alkenes catalyzed by heteropolyoxometalate as pillars in layered double hydroxides", Journal of Molecular Catalysis A: Chemical 145 (1999) 281-289.

R. Jin et al., Selective Oxidation of Cyclopentene to Glutaraldehyde by $H_2O_2$ over the $WO_3/SiO_2$ Catalyst, Journal of Catalysis 203, p. 75-81 (2001).

Z. Zhang et al., "Synthesis, characterization, and catalytic testing of W-MCM-41 mesoporous molecular sieves", Applied Catalysis A: General 179 (1999) 11-19.

R. Neumann et al., "Metal Oxide ($TiO_2$, $MoO_3$, $WO_3$) Substituted Silicate Xerogels as Catalysts for the Oxidation of Hydrocarbons with Hydrogen Peroxide", Journal of Catalysis 166, 206-217 (1997) Artical No. CA971479.

Office Action issued on Mar. 10, 2008 in counterpart European Application No. 03291769.2.

*Primary Examiner*—Taylor Victor Oh
(74) *Attorney, Agent, or Firm*—Connolly Bove Lodge & Hutz LLP

(57) ABSTRACT

The present invention is to provide a method by which, in carrying out a liquid-phase oxidation reaction using a catalyst comprising a tungsten species as an essential component, the catalytic activity performance can be improved or maintained and by which the catalyst component tungsten species can be prevented from being leached into liquid reaction mixtures to thereby control decrease in catalytic activity and make it possible to reuse the catalyst.

A method of liquid-phase oxidation reaction using a tungsten species, wherein that, in carrying out said method of liquid-phase oxidation reaction using a catalyst comprising a tungsten species as an essential component, said tungsten species is caused to be supported on a porous support and, further, a third element other than the component elements of said porous support and the tungsten element is caused to coexist in said catalyst.

10 Claims, No Drawings

LIQUID PHASE OXYGENATION REACTION USING TUNGSTEN SPECIES

TECHNICAL FIELD

The present-invention relates to a method of liquid-phase oxidation reaction using a tungsten species and, more particularly, to a method of liquid-phase oxidation reaction using a tungsten species in which, in carrying out the method of liquid-phase oxidation reaction using a catalyst comprising a tungsten species as an essential component, the catalytic activity performance of the catalyst component can be improved or maintained.

BACKGROUND ART

Tungsten species, which are compounds containing a tungsten atom or atoms as an essential component, show catalytic activity in various reactions and are effective as catalyst components. For example, it is known that supported materials prepared by supporting tungsten species on a support such as alumina, and so on can be used as catalysts for petroleum cracking or alkene isomerization/disproportionation in vapor phase reactions, and it is disclosed that catalysts comprising tungsten oxide supported on a support such as MgO, and so on are useful in 1-butene isomerization and in disproportionation of 1-butene, propylene and ethylene (see e.g. T. Yamaguchi et al, J. Catal., (1987), 65 p. 442-447) There is also a disclosure about the use of alumina-supported tungsten oxide as a catalyst for petroleum cracking (see e.g. L. L. Murrell et al, J. Catal., (1987), 107 p. 463-470).

On the other hand, the method of producing epoxy compounds by carrying out, in the liquid phase, the epoxidation reaction of compounds having at least one ethylenic double bond using an alumina-supported tungsten catalyst and hydrogen peroxide as an oxidizing agent is a useful method and, concerning this method, it is disclosed as follows.

Referring to the method of producing epoxy compound by reacting ethylenic double bond-containing compounds with hydrogen peroxide, it is disclosed that the epoxidation reaction was carried out at 60° C. using allyl alcohol and hydrogen peroxide in a mole ratio of 1.5:1, with a water-hydrogen peroxide mole ratio of 35:1, and using a tungsten species as a supported catalyst (see e.g. U.S. Pat. No. 2,870,171 (specification, columns 2-3, 5, and 8-9)). It is described that, in this epoxidation reaction, the yield was 27 to 31% as expressed in terms of mole percent relative to hydrogen peroxide, with the conversion of hydrogen peroxide of 97.8 to 99.1%. As the supported catalyst, there are mentioned, as tungsten species, $H_2WO_4$, $NaHWO_4$, $NH_4HWO_4$, $Na_2WO_4$, heteropolytungstic acid, heteropolytungstic acid alkali metal or alkaline earth metal salts, and so on, and, as supports, mention is made of alumina, active carbon, magnesia, zirconia, silica-alumina, and clay. Furthermore, $H_2WO_4/Al_2O_3$ (uncalcined) is mentioned in an embodiment.

Furthermore, it is disclosed that compounds represented by $Q_3XW_4O_{24-2n}$ (wherein Q represents the cation of a quaternary onium salt, X represents a P or As atom, and n represents 0, 1 or 2) are supported on an inert substance, such as alumina, for use as catalysts for epoxidation of olefinic compounds using hydrogen peroxide (see e.g. Laid-open European Patent Application No. 0109273 (specification, pages 13-16, 40)).

Referring to the epoxidation reaction using hydrogen peroxide and tungsten catalysts, it is disclosed that cyclohexene, cyclooctene or 1-octene was used as a substrate and subjected to epoxidation reaction at 60° C. in methanol or tert-butanol as a solvent in a substrate-hydrogen peroxide mole ratio of 1:1 or 1:2 (see e.g. International Laid-open Patent Application No. 93/00338 (pamphlet, pages 16-23, 24). It is described that, in this epoxidation reaction, the conversion amounted to 23-98.1% as expressed in terms of mole percent of substrate and the selectivity for epoxidation to 7-92% as expressed in terms of mole percent of substrate. As for the supported catalysts, mention is made of, as tungsten species, tungsten-containing heteropolyacids, such as $M_3PW_nMo_{12-n}O_{40}$ (M representing a counter anion), and, in the embodiments, there are mentioned $H_3PW_{12}O_{40}$—$Al_2O_3$, $H_3PWMo_{11}O_{40}$—$Al_2O_3$, $H_3PW_{12}O_{40}$—Mg silicate, $(CP)_3PW_{12}O_{40}$—$Al_2O_3$, $H_3PW_{12}O_{40}$—$ZrPO_4$, $H_3PW_{12}O_{40}$—$SnO_2$, $H_3PW_{12}O_{40}$—$Al(OH)_3$, $H_3PW_{12}O_{40}$—$TiO_2$, $H_3PW_6Mo_6O_{40}$—$Al_2O_3$, $H_3PMO_{12}O_{40}$—$SiO_2$, and so on. As for the supports, mention is made of solids containing elements selected from the groups IIa, IIb, IIIb, IVa and IVb or organic-based materials such as strong basic resins and, in an embodiment, $Al_2O_3$ is mentioned.

In commercial production processes, such catalysts are generally to be reused. Since, however, the catalyst component tungsten species are leached into liquid reaction mixtures and the catalytic activity decreases accordingly, it becomes impossible to reuse the catalysts. Tungsten species are expensive and, therefore, it is desired that the catalysts be rendered reusable. Although it is disclosed that catalyst calcination (see e.g. International Laid-open Patent Application No. 93/00338 (pamphlet, pages 16-23 and 24)) results in reducing catalyst component leaching as compared with the case of no catalyst calcination (see e.g. U.S. Pat. No. 2,870, 171 (specification, columns 2-3, 5, and 8-9)), there is still room for contrivance for making it possible to suppress the leaching of catalyst components by some methods other than such a method as mentioned above.

Furthermore, when these catalysts are used, the efficiency of hydrogen peroxide utilization as expressed in terms of the percentage of the portion of hydrogen peroxide consumed for epoxy compound formation relative to the whole amount of hydrogen peroxide used as a reactant is low. Therefore, there is room for contrivance from the viewpoint of improving or maintaining the catalytic activity performance as well.

Meanwhile, there is a report about the analyses of the molecular structures of alumina-supported tungsten oxide catalysts with and without addition of a secondary component metal oxide (see e.g. M. M. Ostromecki et al, J. Mol. Catal., A: Chemical, (1998), 132 p. 43-57). Thus, for $WO_3/Al_2O_3$, which has been used for long as a petroleum cracking catalyst, analysis was performed of the manner of supporting of metal oxide additives (the metal being Ni, Fe, P, Sn, La, Co, Ce, Zn, etc.) added to this catalyst on the surface thereof. However, there is no disclosure about the use thereof in actual reactions. Thus, there is no disclosure about the possibility of such catalysts being useful in liquid-phase oxidation reactions. Therefore, there is no description of how to prevent catalyst components from leaching and/or improve or maintain the catalytic activity performance in catalytic reactions.

Further, the epoxidation reaction of cyclooctene with hydrogen peroxide has been disclosed in which a catalyst comprising silicon oxide and tungsten oxide supported on MCM-41 (mesoporous molecular sieve) (see e.g. Briot, E. et al, J. Mater. Chem., (2000), 10 p. 953-958). It is described that this epoxidation reaction was carried out using two or more catalysts prepared by different methods of catalyst preparation or by varying the ratio between the silicon species and tungsten species, using the substrate cyclooctene and hydrogen peroxide in a ratio of 1:5, and using tert-butanol as a solvent, to give substrate conversion of 33-98%. As for the supported catalysts, WO(O$_2$)$_2$(H$_2$O)$_2$ and the like are mentioned as the tungsten species, and MCM-41 is mentioned as the support.

The epoxidation reaction of 1-octene with hydrogen peroxide using a catalyst comprising a tungsten species supported on a hydrophobic mesoporous silica gel has been disclosed (see e.g. T. Sakamoto et al, Tetrahedron Letters, (2000), 41 p. 10009-10012). It is described that this epoxidation reaction was carried out at 90° C., using the substrate 1-octene and hydrogen peroxide in a ratio of 1:2, and using two or more catalysts comprising a tungsten species supported on a silica gel support surface-treated with a silane coupling agent and an alkylating agent to give substrate conversion of 18-100%. As for the supported catalysts, [Π-C$_5$H$_5$N$^+$ (CH$_2$)$_{15}$CH$_3$]$_3$(PW$_{12}$O$_{40}$)$^{3-}$ is mentioned as the tungsten species, and SiO$_2$ surface-treated with Ph$_3$SiOC$_2$H$_5$ and (CH$_3$)$_2$NCH(OCH$_2$Ph)$_2$, among others, is mentioned as the support.

The epoxidation reaction of cyclohexene with hydrogen peroxide has been disclosed in which a catalyst comprising a tungsten species supported on a layered support (see e.g. Watanabe, Y. et al, J. Mol. Catal., A: Chemical, (1999), 145 p. 281-289). It is described that this epoxidation reaction was carried out at a temperature of 70° C., using the substrate cyclohexene and hydrogen peroxide in a ratio of 1:1, and using a catalyst comprising K$_8$SiW$_{11}$O$_{39}$ or K$_4$SiW$_{12}$O$_{40}$ as the tungsten species supported on Zn$_3$Al as the support to give a turnover number of 14 or 1.9 mol/mol-W, respectively.

However, even in the cases where these catalysts are used, there is room for contrivance for preventing the catalyst component tungsten species from being leached into liquid reaction mixtures while maintaining the catalytic activity and efficiency of hydrogen peroxide utilization at high levels.

Further, when efficiency of hydrogen peroxide utilization is low and a catalyst comprising a tungsten species supported on a layered support is used (see e.g. Watanabe, Y. et al. J. Mol. Catal., A: Chemical, (1999), 145 p. 281-289), impurities are formed as byproducts in relatively large amounts and, furthermore, the activity of tungsten species, when supported on such a support, decreases. Thus, there is room for contrivance for making improvements in these respects and thereby improving and maintaining the catalytic activity performance.

SUMMARY OF THE INVENTION

It is an object of the present invention, which has been made in view of the above-mentioned state of the art, to provide a method by which, in carrying out a liquid-phase oxidation reaction using a catalyst comprising a tungsten species as an essential component, the catalytic activity performance can be improved or maintained and by which the catalyst component tungsten species can be prevented from being leached into liquid reaction mixtures to thereby control decrease in catalytic activity and make it possible to reuse the catalyst.

In the course of various investigations concerning the catalysts for use in the methods of liquid-phase oxidation reactions, the present inventors, paying attention to the fact that catalysts comprising a porous support and a tungsten species as essential components, in which the tungsten species provides active sites, are effective in the methods of liquid-phase oxidation reactions, found that when the coexistence, in those catalysts, of a specific element other than the essential components, namely the porous support and tungsten element, is effective in improving or maintaining the catalytic activity performance and, further, in preventing the catalyst component tungsten species from being leached into liquid reaction mixtures, with the result that the catalysts can be prevented from decreasing in catalytic activity and therefore can be reused to a greater extent. Thus, they came to realize that the above object could be successfully accomplished. Such and other findings have now led to completion of the present invention. Whereas, in Ostromecki et al., J. Mol. Catal. A: Chemical, (1998), 132, p. 43-57, there is a report of the molecular structure analysis of catalysts comprising a tungsten oxide supported on alumina with and without addition of another metal oxide, there is no disclosure about the possibility of those catalysts being useful in liquid-phase oxidation reactions. In the prior art, there is no description of adding a third component to the catalysts to be used in carrying out liquid-phase oxidation reactions, and no studies have so far been made on how to improve or maintain the catalytic activity performance or how to prevent the leaching of catalyst components into liquid reaction mixtures. On the contrary, the present invention consists in an industrially useful method by which expensive tungsten species can be efficiently utilized and/or reused, and the method has advantageous effects in that the catalytic activity performance can be improved or maintained in carrying out liquid-phase oxidation reactions and in that the decrease in catalytic activity can be suppressed, hence the catalysts can be reused more efficiently.

Thus, the present invention lies in carrying out a method of liquid-phase oxidation reaction using a catalyst comprising a tungsten species as an essential component as supported on a porous support and further comprising a third element other than component elements of the above-mentioned porous support and the tungsten element as caused to coexist in the above-mentioned catalyst.

DISCLOSURE OF THE INVENTION

In the following, the present invention is described in detail.

The liquid-phase oxidation reaction in which a tungsten species is used in accordance with the present invention is carried out using a catalyst comprising the tungsten species as an essential component. Such liquid-phase oxidation reaction includes (1) unsaturated bond oxidation (oxidation of an unsaturated double bond or unsaturated triple bond of an alkene or alkyne), (2) hydroxyl group oxidation, (3) hetero atom oxidation (oxidation of a sulfur atom, a nitrogen atom, etc.), (4) alkane oxidation, (5) aromatics oxidation, and (6) other oxidation reactions than (1) to (5), among others. More preferred are liquid-phase oxidation reactions using hydrogen peroxide as the oxidizing agent.

Referring to the above-mentioned (1) unsaturated bond oxidation (oxidation of an unsaturated double bond or unsaturated triple bond of an alkene or alkyne), the oxidation of an unsaturated double bond of an alkene includes, among others, epoxidation, ketone formation from an alkene (Wacker oxidation), dihydroxyl compound formation from an alkene, α-hydoxylketone formation from an alkene, alkene cleavage, allyl position oxidation, oxidative cleavage, and ammoxidation.

The oxidation of an unsaturated triple bond of an alkyne includes, among others, α,β-epoxy ketone formation from an alkyne, and diketone formation from an alkyne.

Referring to the above-mentioned (2) hydroxyl group oxidation, there may be mentioned, for example, carbonyl compound formation reactions and, more specifically, aldehyde formation from a primary alcohol, carboxylic acid formation from an aldehyde, and ketone formation from a secondary alcohol, among others.

Referring to the above-mentioned (3) hetero atom oxidation (oxidation of a sulfur atom, a nitrogen atom, etc.), the sulfur atom oxidation includes, for example, sulfoxide formation from a sulfide, sulfone formation from a sulfoxide, and disulfide formation from a thiol.

The nitrogen atom oxidation includes, for example, hydroxylamine formation from a primary amine, nitroso or azoxy compound formation from a hydroxylamine, oxime or nitro compound formation from a nitroso compound, hydroxylamine formation from a secondary amine, nitrone formation from a hydroxylamine, and amine oxide formation from a tertiary amine.

The above-mentioned (4) alkane oxidation includes, among others, reactions by which a hydroxyl, hydroperoxy, alkylperoxy, carboxyl or carbonyl group is introduced into an alkane, and ammoxidation.

The above-mentioned (5) aromatics oxidation includes, for example, nuclear hydroxylation, side chain oxidation, and so on.

As the above-mentioned (6) oxidation reactions other than (1) to (5), there may be mentioned, for example, the Baeyer-Villiger oxidation leading to lactone formation from a ketone, oxidative coupling, and oxidative dehydrogenation.

Usable as the oxidizing agent in the above-mentioned liquid-phase oxidation reactions are, for example, those capable of forming an oxygen ion, oxygen radical, peroxide, or superperoxide, including molecular oxygen, hydrogen-peroxide, cumene hydroperoxide, tert-butyl hydroperoxide, peracetic acid, other organic peroxides, oxygen-hydrogen mixed gases, dinitrogen monoxide, and iodosylbenzene, among others.

Among the above-mentioned various liquid-phase oxidation reactions and oxidizing agents, oxidation reactions in which hydrogen peroxide($H_2O_2$) is used are preferred in the manner of the present invention. Also preferred are oxidation reactions of compounds having at least one ethylenic double bond, by which epoxy compounds can be produced. The production of epoxy compounds by subjecting compounds having at least one ethylenic double bond to oxidation reaction with hydrogen peroxide constitutes one of the preferred embodiments of the present invention.

In carrying out the method of liquid-phase oxidation reaction using a tungsten species in accordance with the present invention, the above-mentioned tungsten species is supported on a porous support and, further, a third element other than the porous support component elements and tungsten element is caused to coexist in the above-mentioned catalyst. Preferably, a third element other than the porous support component elements and tungsten species component elements is caused to coexist in the above-mentioned catalyst. Thus, the catalyst to be used in accordance with the present invention preferably comprises a support and a tungsten species as essential components and further comprising at least one element (third element) other than the elements constituting the essential components. In the practice of the present invention, one or two or more of such catalysts may be used.

In carrying out the method of liquid-phase oxidation reaction using a catalyst comprising a tungsten species as an essential component, the use of such catalyst according to the present invention makes it possible to prevent the tungsten species from being leached and, in certain instances, improve or maintain the catalytic activity performance.

In a preferred embodiment of the above-mentioned catalyst, the third element comprises at least one element selected from the group consisting of the elements of the groups 2, 3, 4, 5, 7, 8, 9, 10, 11, 12, 13, 14, 15, 16 and 17. More preferably, the third element comprises at least one element selected from the group consisting of the elements of the groups 2, 3, 4, 5, 7, 8, 12, 13, 14, 15 and 17. Still more preferably, it comprises at least one element selected from the group consisting of the elements of the groups 2, 3, 7, 8, 12, 13, 14 and 15. More specifically, the element preferably comprises at least one element selected from the group consisting of Mg, Ca, La, Ti, V, Nb, Re, Fe, Zn, Al, In, Sn, Pb, P, Sb, Bi and F, more preferably at least one element selected from the group consisting of La, Zn, Al, Sn, Pb, P, Sb and Bi, still more preferably at least one element selected from the group consisting of La, Zn, Sn, Pb and P.

The "groups" so referred to herein are the groups in the long-period type periodic table consisting of 18 groups.

When the methods of liquid-phase oxidation reactions are carried out in accordance with the present invention, the catalytic activity performance is beneficially improved or maintained and/or the tungsten species leaching is beneficially inhibited and, according to the third element selected, the catalytic activity performance is effectively improved or maintained, or the tungsten species leaching is effectively inhibited, or both of these effects are produced.

In case the catalytic activity performance is effectively improved or maintained, the third element comprises at least one element selected from the group consisting of the elements of the groups 3, 4, 5, 7, 8, 9, 10, 11, 12, 13, 14, 15, 16 and 17. More preferably, the third element comprises at least one element selected from the group consisting of the elements of the groups 3, 4, 7, 8, 12, 13, 14, 15 and 17. In case the tungsten species leaching is effectively inhibited, the third element comprises at least one element selected from the group consisting of the elements of the groups 2, 3, 4, 7, 8, 12, 13, 14, 15, 16 and 17. More preferably, the third element comprises at least one element selected from the group consisting of the elements of the groups 2, 3, 7, 8, 12, 14 and 15.

In the present invention, the third element is preferably selected according to the oxidizing agent used in the method of liquid-phase oxidation reaction. In case hydrogen peroxide is used as the oxidizing agent, a preferred embodiment of the present invention is the third element comprises at least one element selected from the group consisting of the elements of the groups 2, 3, 4, 5, 7, 12, 13, 14, 15, 16 and 17. More preferably, the third element comprises at least one element selected from the group consisting of the elements of the groups 2, 3, 7, 12, 13, 14, 15 and 17. More specifically, the element preferably comprises at least one element selected from the group consisting of Mg, Ca, La, Ti, V, Nb, Re, Zn, Al, In, Sn, Pb, P, Sb, Bi and F, more preferably at least one element selected from the group consisting of La, Zn, Al, Sn, Pb and P.

In case oxygen is used as the oxidizing agent, a preferred embodiment of the present invention is the third element comprises at least one element selected from the group consisting of the elements of the groups 3, 4, 5, 7, 8, 9, 10, 11, 12, 14, 15, 16 and 17. More preferably, the third element comprises at least one element selected from the group consisting of the elements of the groups 3, 4, 5, 7, 8, 9, 10, 11 and 12. More specifically, the element preferably comprises at least one element selected from the group consisting of La, Ti, V, Mn, Fe, Ru, Co, Ni, Pb, Cu, and Zn, more preferably at least one element selected from the group consisting of La, Fe and Zn.

In a preferred embodiment, the above-mentioned catalyst comprises a tungsten species and a third element, both supported on a porous support. While the above-mentioned catalyst preferably comprises a porous support, a tungsten species, and a third element as main components, it may contain an impurity or impurities formed in the process of catalyst preparation and/or a further component(s) unless the effects of the present invention are impaired.

The porous support, one of the essential components of the above-mentioned catalyst, includes alumina ($Al_2O_3$), zirconia ($ZrO_2$), titania ($TiO_2$), silica, clay, zinc oxide, tin oxide, magnesium oxide, lanthanum oxide, barium oxide, hydrotalcite, activated carbon, tungsten oxide, zinc phosphate, lead phosphate, lanthanum phosphate, zeolite, ion exchange resins, and composite oxides such as silica-alumina, tungsten oxide-tin oxide and tin oxide-alumina, and so forth. One or two or more of these may be used. Among them, alumina or tin oxide is preferably used as an essential component. As for the tungsten species, any of those compounds which contain at least one tungsten atom as an essential component and can provide active sites in carrying out a method of liquid-phase oxidation reaction in a liquid reaction mixture can be used. The term "porous support component" so referred to herein denotes an element contained in the porous support and accounting for at least 0.05 part by weight per 100 parts by weight of the porous support.

In carrying out a method of liquid-phase oxidation reaction using a catalyst comprising a tungsten species as an essential component in accordance with a preferred mode of embodiment of the present invention, the tungsten species is supported on a porous support and, at the same time, at least one element selected from the group consisting of Mg, Ca, La, Re, Fe, Zn, Al, In, Sn, Pb, P, Sb, Bi and F other than the porous support components and tungsten element is caused to coexist in the catalyst.

More preferred is a method of liquid-phase epoxidation reaction carried out in the presence of a catalyst prepared by supporting a tungsten species on a porous support comprising alumina and/or tin oxide as an essential component(s) and further causing at least one element selected from the group consisting of La, Zn, Al, Sn and Pb other than the porous support components and tungsten element to coexist in the catalyst.

The tungsten species content in the above-mentioned catalyst may be appropriately selected according to the type or kind of liquid-phase oxidation reaction in which the catalyst is used, the tungsten species and other factors. Preferably, it is not less than 0.1 part by weight but not more than 50 parts by weight per 100 parts by weight of the porous support. More preferably, it is not less than 1 part by weight but not more than 40 parts by weight. The third element content may be adequately selected according to the kind of tungsten species, the third element species, and so forth. Preferably, it is not less than 0.01 part by weight but not more than 1,000 parts by weight per 100 parts by weight of the tungsten species. More preferably, it is not less than 0.1 part by weight but not more than 800 parts by weight.

The above-mentioned catalyst can be prepared by causing the tungsten species and third element to be supported on the porous support. As the supporting method, there may be mentioned (1) the method causing the third element to be supported on the support prior to supporting of the tungsten species, (2) the method causing the third element to be supported on the support after supporting of the tungsten species, and (3) the method causing the tungsten species and third element to be simultaneously supported on the support. The solvent to be used in catalyst preparation, the pH thereof, and the preparation temperature may be appropriately selected according to the porous support species, tungsten species, and third element, among others. Preferably, the catalyst is prepared at 0° C. to 95° C. using an aqueous solvent-or water-containing organic solvent adjusted to pH 0.5 to 12. In preparing the catalyst in accordance with the present invention, calcination is preferably carried out after supporting of the tungsten species and third element on the porous support. By doing so, it becomes possible to further improve the catalytic activity performance and/or further inhibit the tungsten species leaching and thereby facilitate the reuse of the catalyst.

The calcination temperature in such catalyst preparation is preferably within the range of 300 to 800° C. Such catalysts calcined at a temperature of 300-800° C. are suitable as the catalyst to be used in the practice of the present invention. The calcination temperature is more preferably not lower than 330° C. but not higher than 700° C. The calcination time is preferably within the range of from 30 minutes to 24 hours, more preferably from 40 minutes to 20 hours. The gaseous atmosphere during calcination is not particularly restricted but may be air, nitrogen, argon or oxygen, for instance. Air is preferred, however.

Suitable as the compound to be used for tungsten species supporting in the above-mentioned catalyst preparation method are tungstic acid and salts thereof, and salts of tungsten atom-containing heteropolyoxometallate anions. Suitable as the compound for third element supporting are third element-containing acids and salts thereof and, among them, the acids and chloride, nitrate and acetate salts are preferred. These may be used singly or two or-more of them may be used in combination.

Suitable as the above-mentioned tungstic acid and salts thereof are $H_2WO_4$, $Na_2WO_4$, $NaHWO_4$, $(NH_4)_2WO_4$, $NH_4HWO_4$, $(NH_4)_{10}[W_{12}O_{41}]$, $[WO(O_2)_2(H_2O)_2]$, $K_2[WO(O_2)_2(H_2O)_2]_2O$, $Na_2[WO(O_2)_2(H_2O)_2]_2O$, and the like. Preferred as the tungsten atom-containing heteropolyoxometallate anions are Keggin-structured heteropolyoxometallate anions represented by the general formula (1):

$$[XW_nO_m]^{q-} \qquad (1)$$

wherein X represents a silicon atom or phosphorus atom; (n, m) are (12, 40) when there is no deficiency, (11, 39) when there is one deficient structure site, (10, 36) when there are two deficient structure sites, or (9, 34) when there are three deficient structure sites, and q is a positive integer. The value of q is determined by the valence of the element X. Among them, $[\gamma\text{-}SiW_{10}O_{36}]^{8-}$, $[PW_{12}O_{40}]^{3-}$, $[PW_9O_{34}]^{9-}$, $[SiW_{12}O_{40}]^{4-}$ are preferred. When a deficient type heteropolyoxometallate is utilized, it may have another element or elements incorporated or coordinated in the one, two or three deficient sites.

Suitable as the cation to form a salt with the heteropolyoxometalate anion are, for example, proton, alkali metal cations (lithium ions, sodium ions, potassium ions, rubidium ions, cesium ions), alkaline earth metal cations (beryllium ions, magnesium ions, calcium ions, strontium ions, barium ions), lanthanide ions, zinc ions, aluminum ions, tin ions, lead ions, and organic cation-containing cations such as quaternary ammonium salts (e.g. tetramethylammonium salt, tetraethylammonium salt, tetrapropylammonium salt, tetrabutylammonium salt, tributylmethylammonium salt, trioctylmethylammonium salt, trilaurylmethylammonium salt, benzyltrimethylammonium salt, benzyltriethylammonium salt, benzyltributylammonium salt, tetracetylpyridinium salt, ammonium salt), quaternary phosphonium salts (e.g. tetramethylphosphonium salt, tetraethylphosphonium salt, tetrapropylphosphonium salt, tetrabutylphosphonium salt, tetraphenylphosphonium salt, ethyltriphenylphosphonium salt, benzyltriphenylphosphonium salt), and quaternary arsenium salts. The cation may comprise one single species or two or more species. Among these, proton, sodium ion, potassium ion, zinc ion, ammonium ion, and tetrabutylammonium salt are preferred.

In carrying out the methods of liquid-phase oxidation reactions using a catalyst comprising a tungsten species as an essential component, the methods provided by the present invention are effective in efficiently improving or maintaining the catalyst activity performance and/or in efficiently preventing the tungsten species from being leached, as mentioned above. In those methods, however, the catalyst activity performance range and the tungsten species leaching range vary according to the tungsten species and the manner of the method of liquid-phase oxidation reaction.

As for the above-mentioned method of effectively inhibiting tungsten species leaching, it is only required that the leaching (mole percent) of the catalyst-supported tungsten species into liquid reaction mixtures be reduced as compared with the form containing no third element other than the porous component components and tungsten element. In that case, when the tungsten species leaching from the third element-free catalyst is taken as 100 mole percent, a reduction in leaching by only 1 mole percent may be regarded as advantageous from the viewpoint of efficient utilization of tungsten, which is expensive, hence that leaching should preferably be not more than 99 mole percent, more preferably not more than 80 mole percent, still more preferably not more than 60 mole percent, most preferably not more than 40 mole percent.

Regarding the above-mentioned leaching preventing method, the extent of inhibition of tungsten species leaching in each solvent form to be used in each respective reaction should preferably be such that when the tungsten species leaching from the third element-free catalyst is taken as 100 mole percent, the leaching be not more than 99 mole percent, more preferably not more than 60 mole percent when a water solvent is used. When a water-containing organic solvent is used, it is preferably not more than 99 mole percent, more preferably not more than 40 mole percent. Further, when an organic solvent is used, it is preferably not more than 99 mole percent, more preferably not more than 20 mole percent.

In cases where a third component-free, non-leaching-inhibited catalyst is used repeatedly, the difference in cumulative tungsten species leaching between that catalyst and third component-containing catalyst increases with the increasing number of repetitions of use. For example, when a catalyst showing a relative rate of leaching of 99% is used repeatedly, the differences as compared with the non-leaching-inhibited catalyst will be as follows. After one run, the tungsten species leaching for the third element-containing, leaching-inhibited catalyst is expected to be 0.99, with that for the third element-free catalyst being taken as 1, and the cumulative tungsten species leaching after two runs to be $(0.99)^2$ (second power of 0.99) for the third element-containing, leaching-inhibited catalyst, with that for the third element-free catalyst being taken as 1, hence the cumulative tungsten species leaching after n repeated runs is expected to be $(0.99)^n$ (nth power of 0.99) for the third element-containing, leaching-inhibited catalyst, with that for the third element-free catalyst being taken as 1. Thus, from the viewpoint of efficient use of expensive tungsten, it is very important to suppress the leaching and reduce the relative rate of leaching, and this is one of the advantageous effects of the present invention.

On that occasion, the $H_2O_2$-based yield of the oxidation reaction product, expressed in terms of mole percent, is preferably not less than 40%, more preferably not less than 60 mole percent. The selectivity toward the epoxy compound, expressed in terms of mole ratio (mole percent) relative to 100 mole percent of the whole reaction product, is preferably not less than 80%, more preferably not less than 90%.

Regarding the above-mentioned method of effectively improving or maintaining the catalytic activity performance, it is required that the yield, efficiency of oxidizing agent utilization, and selectivity, among others, be improved or maintained as compared with the form in which the catalyst contains no coexisting third element other than the porous support components and tungsten element. In the case of epoxidation of an ethylenic double bond-containing compound with hydrogen peroxide, the yield of the epoxidation product, as expressed in terms of mole percent relative to the moles of the ethylenic double bond-containing compound fed as the starting material, is preferably at least 1.3 times, more preferably at least 1.6 times, as compared with the yield obtained with the third element-free catalyst. For example, in the case of epoxidation of 1-butene with hydrogen peroxide, the efficiency of hydrogen peroxide utilization is about 30 to 40% in the prior art whereas when Zn is used as the third element, the rate of the main reaction, namely epoxidation reaction, rises and, accordingly, the proportion of hydrogen peroxide decomposed into water and oxygen prior to the consumption thereof in the epoxidation reaction decreases, so that the efficiency of hydrogen peroxide utilization can be improved to about 70 to 80% and the yield can be increased.

The above-mentioned mole percent of the epoxidation product can be determined by means of gas chromatography. The efficiency of hydrogen peroxide utilization can be calculated from the mole of remaining hydrogen peroxide as determined on a potentiometric titration apparatus and the mole of the oxidation reaction product.

In the following, a description is given of the reaction substrate, manufacturing conditions and other factors to be employed in the production of epoxy compounds by oxidizing compounds having at least one ethylenic double bond with hydrogen peroxide using the catalyst mentioned above as a preferred embodiment of the present invention.

The reactant substrate to be used mentioned above, namely the compound having at least one ethylenic double bond, may be an acyclic or cyclic organic compound and may comprise one or more of hydrocarbons, esters, alcohols, ethers, and halo-substituted hydrocarbons, for instance. Specifically, there may be mentioned straight-chain alkenes having a terminal ethylenic double bond, such as ethylene, propylene, 1-butene, butadienes, 1-hexene, 1-pentene, isoprene, diisobutylene, 1-heptene, 1-octene, 1-nonene, 1-undecene, 1-dodecene, 1-tridecene, 1-tetradecene, 1-pentadecene, 1-heptadecene, 1-octadecene, 1-nonadecene, 1-eicocene, propylene trimer and tetramers, and 1,3-butadiene; alkenes or branched alkenes having an ethylenic double bond in the molecule, such as 2-butene, 2-octene, 2-methyl-2-hexene, and 2,3-dimethyl-2-butene; and alicyclic olefinic hydrocarbons such as cyclopentene, cyclohexene, 1-phenyl-1-cyclohexene, 1-methyl-1-cyclohexene, cycloheptene, cyclooctene, cyclodecene, cyclopentadiene, cyclodecatriene, cyclooctadiene, dicyclopentadiene, methylenecylopropane, methylenecyclopentane, methylenecyclohexane, vinylcyclohexane, cyclooctene and norbornene, among others. Among these, unsaturated hydrocarbons containing 2 to 15 carbon atoms are preferred. More preferred are unsaturated hydrocarbons containing 2 to 12 carbon atoms.

The compound having at least one ethylenic double bond may also have such a group as —COOH, —CN, —COOR or —OR (R being an alkyl, cycloalkyl, aryl or allylalkyl substituent), or an aryl, allylalkyl, halogen, nitro, sulfo, carbonyl (e.g. ketone or aldehyde), hydroxyl or ether group. As such compound, there may be mentioned, among others, allyl alcohol, allyl chloride, allyl methyl ether, allyl vinyl ether, diallyl ether, allyl phenyl ether, methyl methacrylate, acrylic acid and the like.

Also usable as the above compound having at least one ethylenic double bond are carbon-carbon double bond-containing aryl compounds containing 6 or more carbon atoms. As such compounds, there may be mentioned, among others, styrene, substituted styrenes such as α-methylstyrene, divinylbenzenes, stilbene, aralkenes; carbon-carbon double bond-containing amines, thiols, sulfides, disulfides, Se—, Te—, Sb or As— containing compounds, phosphines and phosphites.

The above-mentioned hydrogen peroxide is preferably used, in the form of a solution in water or alcohols at a concentration of 0.01 to 70% by mass, although 100% hydrogen peroxide can also be used. The amount of the above-mentioned hydrogen peroxide to be used is preferably not less than 100/1, more preferably not less than 10/1, but preferably not more than 1/100, more preferably not more than 1/50, as expressed in terms of mole ratio relative to the ethylenic double bond in the reactant substrate, namely the compound having at least one ethylenic double bond (moles of the ethylenic double bond in the reactant substrate/moles of the $H_2O_2$ agent).

As for the amount of the catalyst used mentioned above, the mole ratio between the ethylenic double bond in the reaction substrate, namely compound having at least one ethylenic bond, to the tungsten species in the catalyst (moles of the ethylenic double bond in the reaction substrate/moles of the tungsten species) is preferably not less than 100,000/1, more preferably not less than 10,000/1. Besides, it is preferably not more than 1/10, more preferably not more than 1/1.

As for the method of reaction in the above-mentioned epoxy compound production, the epoxidation reaction is preferably carried out by bringing the compound having at least one ethylenic double bond and hydrogen peroxide into contact with the catalyst in a solvent. Since a solid catalyst is used in the practice of the present invention, the reaction is carried out in the so-called heterogeneous system, with the catalyst forming a solid phase and the reactants such as reaction substrate and hydrogen peroxide forming a gaseous phase or liquid-phase.

As the solvent for the reaction solution mentioned above, water and/or an organic solvent is used. The organic solvent may comprise one single species or two or more species. Preferred are those which will not react with the compound having at least one ethylenic double bond which is the reactant substrate, the oxidizing agent such as hydrogen peroxide, or the product epoxy compound. As such organic solvent, there may be mentioned, among others, primary, secondary or tertiary monohydric alcohols containing 1 to 6 carbon atoms, such as methanol, ethanol, normal- or isopropanol and tert-butanol; polyhydric alcohols such as ethylene glycol, propylene glycol and glycerol; oligomers resulting from ring opening of ethylene oxide or propylene oxide, such as diethylene glycol and triethylene glycol; ethers such as ethyl ether, isopropyl ether, dioxane and tetrahydrofuran, cyclopenthylmethyl ether; esters such as ethyl acetate and formic acid esters or acetic acid esters of polyhydric alcohols; ketones such as acetone, methyl ethyl ketone, methyl isobutyl ketone and acetylacetone; nitrogen compounds such as dimethylformamide, nitromethane and nitriles; phosphorus compounds, for example phosphate esters such as triethyl phosphate and diethyl hexyl phosphates; halogenated hydrocarbons such as chloroform, dichloromethane and ethylene dichloride; aliphatic hydrocarbons such as n-hexane and n-heptane; aromatic hydrocarbons such as toluene and xylene; and alicyclic hydrocarbons such as cyclohexane and cyclopentane. Preferably used among the solvents mentioned above are water, alcohols containing 1 to 4 carbon atoms, 1,2-dichloroethane, heptane, toluene, xylene, chlorobenzene, acetonitrile, benzonitrile, dimethyl sulfoxide, dimethylformamide and the like, and a mixture of these. A more preferred solvent is water or a mixed solvent composed of water and an organic solvent selected from among methanol, heptane, toluene, acetonitrile and benzonitrile. Still more preferred is a water-organic solvent mixture, since the tungsten species leaching in such mixture is more inhibited as compared with that in water. In cases where water is present, it is also possible to allow a phase transfer catalyst and/or a surfactant to coexistence as the case may be.

In the above epoxidation reaction, it is preferred that the reaction system(reaction solution) be neutral to acidic. Although, in the present invention, the reaction system can be rendered acidic by using the above catalyst, an acidic substance may further be added to the reaction system. Suitable as the acidic substance is a Brønsted acid or a Lewis acid, and may comprise one single species or two or more species. Suitable as the Brønsted acid are, for example, mineral acids such as hydrochloric acid, sulfuric acid, nitric acid, phosphoric acid and boric acid; organic acids such as acetic acid, benzoic acid, formic acid, trichloroacetic acid, trifluoromethanesulfonic acid and sulfonic acid; zeolites, mixed oxides and like inorganic acids. Suitable as the Lewis acid are aluminum chloride, ferric chloride, boron chloride compounds, antimony chloride compounds, stannic chloride, antimony fluoride, zinc compounds, titanium compounds, zeolites, mixed oxides and the like. Furthermore, inorganic or organic acidic salts may also be used.

As for the reaction conditions in the above epoxidation reaction, the temperature, for instance, is preferably not lower than 0° C., more preferably not lower than room temperature, but preferably not higher than 250° C., more preferably not higher than 180° C. The reaction time is preferably not shorter than several minutes but not longer than 150 hours, more preferably not longer than 48 hours. The reaction pressure is preferably not lower than ordinary pressure but not higher than $2 \times 10^7$ Pa, more preferably not higher than $5 \times 10^6$ Pa. It is also possible to carry out the reaction under reduced pressure.

The epoxy compounds produced in accordance with the present invention while preventing the catalytic activity from decreasing and preventing catalyst component leaching into the liquid reaction mixture to enable the reuse of the catalyst are suited for use as intermediates or starting materials in the production of various industrial products. Among the epoxy compounds obtainable by the production method of the present invention, ethylene oxide, which can serve as the raw material for ethylene glycol or polyethylene glycol, and propylene oxide, which can serve as the raw material for the production of polyethers or polyols, are commercially important. These epoxy compounds are also important intermediates for the production of alkylene glycols such as propylene glycol and dipropylene glycol, and alkanolamines, which are important industrial products as raw materials for solvents and surfactants. Among such epoxy compounds, those compounds having a functional group(s) other than an epoxy group within the molecule can be utilized as intermediates from which various derivatives can be synthesized making good use of the reactivity of that functional group(s). For example, glycidol, the product of epoxidation of the double bond of allyl alcohol, is a substance useful as a starting material for the production of glycidyl ethers, glycidyl esters, glycerol ethers, glycerol esters, dihydroxypropylamine, and the like, medicinals and intermediates thereof, paints, adhesives, UV curing agents for semiconductor device, and so forth.

The method of liquid-phase oxidation reaction using the tungsten species in accordance with the present invention has the constitution mentioned above and constitutes a method by which, in carrying out a method of liquid-phase oxidation reaction using a catalyst comprising the tungsten species as an essential component, the catalytic activity performance can be improved or maintained and by which the catalyst component tungsten species can be prevented from being leached into liquid reaction mixtures to thereby control decrease in catalytic activity and make it possible to reuse the catalyst. For example, it is a useful method in producing epoxy compounds suitable as intermediates or starting materials to be used in the production of various industrial products.

BEST MODE FOR CARRYING OUT THE INVENTION

The following examples illustrate the present invention in more detail. These examples are, however, by no means limitative of the scope of the present invention. Unless otherwise specified, "part(s)" means "part(s) by weight", "%" means "mole%".

<Preparation Method 1>
(1) A third element-containing acid or salt (1.3 mmol) was dissolved in 50 mL of water (with hydrochloric acid or nitric acid added when the acid or salt was insoluble in water), 10 g of the support γ-$Al_2O_3$ was added, and the water was distilled off under reduced pressure. The residue was then calcined at 500° C. for 2 hours. Used as the third element-containing acid or salt were phosphoric acid, and/or nitrates, acetates and/or ammonium salts and/or halides of Ca, Sb, Pb, Zn, Sn, La, Bi, and F.
(2) Water (40-50 mL) was added to 1.5 g of $H_2WO_4$, the mixture was heated to 80° C., and the pH was adjusted to 7 by addition of aqueous ammonia. After cooling, the mixture was again heated to 80° C., and the pH was adjusted to 7 by addition of aqueous ammonia.
(3) After cooling to room temperature, the impurities were filtered off.
(4) A 3.0 g portion of the solid obtained in (1) was added to the solution obtained in (3), and the mixture was stirred at 60° C. for 1 hour.
(5) After filtration under reduced pressure, the white solid obtained was dried at 120° C. for 6 hours and then calcined at 400-600° C. for 3 hours.

The thus-prepared catalyst is hereinafter referred to as W/M-$Al_2O_3$ (M=Ca, Sb, Pb, Zn, Sn, P, La, Bi, F)

<Preparation Method 2>
The heteropolyoxometallate $K_8[SiW_{10}O_{36}]\cdot 12H_2O$ was prepared as described in the following reference.
A. Teze et al, Inorg. Synth., (1990), 27 p. 88
(1) Water (40-50 mL) was added to 1.5 g of $K_8[SiW_{10}O_{36}]\cdot 12H_2O$ and the pH was adjusted to 3 with concentrated aqueous nitric acid.
(2) To the solution of (1) was added 3.0 g of the support γ-$Al_2O_3$, and the mixture was stirred at 60° C. for 1 hour.
(3) After filtration under reduced pressure, the white solid obtained was dried at 120° C. for 6 hours and then calcined at 400° C. for 3 hours.
(4) A metal salt (0.39 mmol) was dissolved in 50 mL of water, the whole amount of the solid obtained in (3) was added, and the water was distilled off under reduced pressure. The residue was then dried at 120° C. for 6 hours and then calcined at 400° C. for 3 hours. The thus-prepared catalyst is hereinafter referred to as M/γ-$SiW_{10}O_{36}$/$Al_2O_3$ (M=Pb, Mg, La). Used as the metal salt were nitrates or acetates of Pb, Mg and La.

<Preparation Method 3>
(1) A metal salt (1.3 mmol) was dissolved in 50 mL of water, 10 g of the support γ-$Al_2O_3$ was added, and the water was distilled off under reduced pressure. The residue was then calcined at 500° C. for 2 hours. Used as the metal salt were nitrates of Pb and La.
(2) 35% aqueous hydrogen peroxide (8 mL) was added to 1.5 g of $H_2WO_4$, the mixture was stirred at 60° C. for 1 hour.
(3) Water (20 mL) and the solid obtained in (1) were added to the solution obtained in (2), and the mixture was stirred at 60° C. for 1 hour.
(4) After filtration under reduced pressure, the white solid obtained was dried at 120° C. for 6 hours and then calcined at 400° C. for 3 hours.

The thus-prepared catalyst is hereinafter referred to as $WO(O_2)_2$ $(H_2O)_2$/M-$Al_2O_3$ (M=Pb, La).

<Preparation Method 4>
(1) A third element-containing acid or salt (1.3 mmol) was dissolved in 50 mL of water, 10 g of the support γ-$Al_2O_3$ was added, and the water was distilled off under reduced pressure. The residue was then calcined at 500° C. for 2 hours. Used as the third element-containing acid or salt were nitrates, acetates and/or ammonium salts and/or halides of Sn, Re, In and F.
(2) Water (50 mL) was added to 1.5 g of zinc nitrate, the whole amount of the solid obtained in (1) was added, and the water was distilled off under reduced pressure. The residue was then calcined at 500° C. for 2 hours.
(3) Water (40-50 mL) was added to 1.5 g of $H_2WO_4$, the mixture was heated to 80° C., and the pH was adjusted to 7 by addition of aqueous ammonia. After cooling, the mixture was again heated to 80° C., and the pH was adjusted to 7 by addition of aqueous ammonia.
(4) After cooling to room temperature, the impurities were filtered off.
(5) A 3.0 g portion of the solid obtained in (2) was added to the solution obtained in (4), and the mixture was stirred at 60° C. for 1 hour.
(6) After filtration under reduced pressure, the white solid obtained was dried at 120° C. for 6 hours and then calcined at 400° C. for 3 hours.

The thus-prepared catalyst is hereinafter referred to as W/M-Zn—$Al_2O_3$ (M=Sn, Re, In, F).

<Preparation Method 5>
(1) Zinc nitrate (1.3 mmol) was dissolved in 50 mL of water, 10 g of the support γ-$Al_2O_3$ was added, and the water was distilled off under reduced pressure. The residue was then calcined at 500° C. for 2 hours
(2) Water (40-50 mL) was added to 1.5 g of $H_3PW_{12}O_{40}$, a 3.0 g portion of the solid obtained in (1) was added, and the mixture was stirred at 60° C. for 1 hour.
(3) After filtration under reduced pressure, the white solid obtained was dried at 120° C. for 6 hours and then calcined at 400° C. for 3 hours.

The thus-prepared catalyst is hereinafter referred to as $H_3PW_{12}O_{40}/Zn-Al_2O_3$.

<Preparation Method 6>
(1) A third element-containing acid or salt (6.5 mmol) was dissolved in 200 mL of water, 50 g of the support $SnO_2$ was added, and the water was distilled off under reduced pressure. The residue was then dried at 200° C. for 30 minutes and then calcined at 500° C. for 2 hours. Used as the third element-containing acid or salt were nitrates and/or halides of Zn and Al.
(2) Water (50 mL) was added to 2.5 g of $H_2WO_4$, the mixture was heated to 60° C., and the pH was adjusted to 8 by addition of aqueous ammonia. After cooling, the mixture was again heated to 60° C., and the pH was adjusted to 8 by addition of aqueous ammonia.
(3) After cooling to room temperature, the impurities were filtered off.
(4) A 5.0 g portion of the solid obtained in (1) was added to the solution obtained in (3), and the mixture was stirred at 60° C. for 1 hour.
(5) After filtration under reduced pressure, the solid obtained was dried at 120° C. for 6 hours and then calcined at 400° C. for 2 hours.

The thus-prepared catalyst is hereinafter referred to as W/M-$SnO_2$ (M=Zn, Al).

<Preparation Method 7>
(1) Zinc nitrate (6.5 mmol) was dissolved in 200 mL of water, 50 g of the support $SnO_2$ was added, and the water was distilled off under reduced pressure. The residue was then dried at 200° C. for 30 minutes and then calcined at 500° C. for 2 hours.
(2) Water (40-50 mL) was added to 1.5 g of $H_3PW_{12}O_{40}$, and the pH was adjusted to 6.0 by addition of aqueous ammonia.
(3) A 3.0 g portion of the solid obtained in (1) was added to the solution obtained in (2), and the mixture was stirred at 60° C. for 1 hour.
(4) After filtration under reduced pressure, the solid obtained was dried at 120° C. for 6 hours and then calcined at 400° C. for 3 hours.

The thus-prepared catalyst is hereinafter referred to as $H_3PW_{12}O_{40}/Zn-SnO_2$.

<Preparation Method 8>
The polyanion $[Fe_2SiW_{10}O_{38}]^{6-}$ was prepared as described in the following reference.

Y. Nishiyama et al, Angew. Chem., Int. Ed., (2001), 40 p. 3639-3641

(1) Zinc nitrate (6.5 mmol) was dissolved in 200 mL of water, 50 g of the support $SnO_2$ was added, and the water was distilled off under reduced pressure. The residue was then dried at 200° C. for 30 minutes and then calcined at 500° C. for 2 hours.
(2) Water (30 mL) was added to 1.5 g of $K_8[SiW_{10}O_{36}]\cdot12H_2O$, the pH was adjusted to 3.9 with concentrated nitric acid, a solution of 0.41 g of iron nitrate nonahydrate in 5 mL of water was gradually added dropwise, and the mixture was stirred for 10 minutes.
(3) To the solution of (2) was added the solid obtained in (1) or 3.0 g of $SnO_2$, and the mixture was stirred at 60° C. for 1 hour.
(4) After filtration under reduced pressure, the solid obtained was dried at 120° C. for 6 hours and then calcined at 400° C. for 2 hours. The thus-prepared catalyst is hereinafter referred to as $\gamma\text{-}Fe_2SiW_{10}O_{38}/Zn-SnO_2$ or $\gamma\text{-}Fe_2SiW_{10}O_{38}/SnO_2$.

EXAMPLES 1 TO 13 AND COMPARATIVE EXAMPLES 1 TO 3

[Hydrogen Peroxide Oxidation Reaction of Allyl Alcohol]

The hydrogen peroxide oxidation of allyl alcohol was carried out under the following conditions using the catalysts obtained in Preparation Methods 1 to 3. The results are shown in Tables 1 to 3.

| Allyl alcohol: | 10 mmol |
| Aqueous hydrogen peroxide: | 2 mmol |
| Water: | 2 mL |
| Reaction temperature: | 60° C. |
| Reaction time: | 2 hours |
| Catalyst: | 100 μmol |

TABLE 1

| | Catalyst | $H_2O_2$-based yield (%) | Selectivity (%) Glycidol | Selectivity (%) Acrolein | Tungsten leaching (%) | Relative rate of leaching (%) |
|---|---|---|---|---|---|---|
| Example 1 | $W/Ca-Al_2O_3$ | 71 | 91 | 9 | 0.90 | 95.7 |
| Example 2 | $W/Sb-Al_2O_3$ | 68 | 91 | 9 | 0.51 | 54.2 |
| Example 3 | $W/Pb-Al_2O_3$ | 66 | 93 | 7 | 0.098 | 10.4 |
| Example 4 | $W/Zn-Al_2O_3$ | 66 | 90 | 10 | 0.90 | 95.7 |
| Example 5 | $W/Sn-Al_2O_3$ | 63 | 91 | 9 | 0.32 | 34.0 |
| Example 6 | $W/P-Al_2O_3$ | 62 | 91 | 9 | 0.23 | 24.5 |
| Example 7 | $W/La-Al_2O_3$ | 53 | 92 | 8 | 0.18 | 19.1 |
| Example 8 | $W/Bi-Al_2O_3$ | 44 | 90 | 10 | 0.52 | 55.3 |
| Compar. Ex. 1 | $W/Al_2O_3$ | 73 | 92 | 8 | 0.94 | — |

TABLE 2

| Catalyst | $H_2O_2$-based yield (%) | Selectivity (%) Glycidol | Acrolein | Tungsten leaching (%) | Relative rate of leaching (%) |
|---|---|---|---|---|---|
| Example 9 | Pb/γ-SiW$_{10}$O$_{36}$/Al$_2$O$_3$ | 66 | 89 | 11 | 2.5 | 14.2 |
| Example 10 | Mg/γ-SiW$_{10}$O$_{36}$/Al$_2$O$_3$ | 58 | 94 | 6 | 7.0 | 39.8 |
| Example 11 | La/γ-SiW$_{10}$O$_{36}$/Al$_2$O$_3$ | 54 | 87 | 13 | 3.6 | 20.5 |
| Compar. Ex. 2 | γ-SiW$_{10}$O$_{36}$/Al$_2$O$_3$ | 73 | 90 | 10 | 17.6 | — |

TABLE 3

| Catalyst | $H_2O_2$-based yield (%) | Selectivity (%) Glycidol | Acrolein | Tungsten leaching (%) | Relative rate of leaching (%) |
|---|---|---|---|---|---|
| Example 12 | WO(O$_2$)$_2$(H$_2$O)$_2$/Pb—Al$_2$O$_3$ | 63 | 90 | 10 | 0.015 | 37.5 |
| Example 13 | WO(O$_2$)$_2$(H$_2$O)$_2$/La—Al$_2$O$_3$ | 53 | 91 | 9 | 0.03 | 75.0 |
| Compar. Ex. 3 | WO(O$_2$)$_2$(H$_2$O)$_2$/Al$_2$O$_3$ | 63 | 93 | 7 | 0.04 | — |

EXAMPLES 14 TO 27 AND COMPARATIVE EXAMPLES 4 TO 5

[Hydrogen Peroxide Oxidation Reaction of 1-butene]

The hydrogen peroxide oxidation of 1-butene was carried out under the following conditions using the catalysts obtained in Preparation Methods 1 and 4 to 7. The results are shown in Table 4.

| 1-butene: | bubbling for 10 minutes |
|---|---|
| Aqueous hydrogen peroxide: | 1 mmol |
| Benzonitrile: | 6 mL |
| Reaction temperature: | 60° C. |
| Reaction time: | 2 hours |
| Catalyst: | 100 μmol |

TABLE 4

| Catalyst | | Calcination temperature (° C.) | $H_2O_2$-based yield (%) | Efficiency of $H_2O_2$ utilization (%) |
|---|---|---|---|---|
| Example 14 | W/Zn—Al$_2$O$_3$ | 400 | 54 | 56 |
| Example 15 | W/Zn—Al$_2$O$_3$ | 500 | 57 | 61 |
| Example 16 | W/Zn—Al$_2$O$_3$ | 600 | 55 | 57 |
| Example 17 | W/La—Al$_2$O$_3$ | 400 | 45 | 46 |
| Example 18 | W/F—Al$_2$O$_3$ | 400 | 37 | 41 |
| Example 19 | W/Sn—Al$_2$O$_3$ | 400 | 42 | 44 |
| Example 20 | W/F—Zn—Al$_2$O$_3$ | 400 | 46 | 48 |
| Example 21 | W/In—Zn—Al$_2$O$_3$ | 400 | 45 | 46 |
| Example 22 | W/Re—Zn—Al$_2$O$_3$ | 400 | 43 | 45 |
| Example 23 | W/Sn—Zn—Al$_2$O$_3$ | 400 | 41 | 45 |
| Example 24 | H$_3$PW$_{12}$O$_{40}$/Zn—Al$_2$O$_3$ | 400 | 41 | 44 |
| Example 25 | W/Zn—SnO$_2$ | 400 | 63 | 71 |
| Example 26 | W/Al—SnO$_2$ | 400 | 73 | 81 |
| Example 27 | H$_3$PW$_{12}$O$_{40}$/Zn—SnO$_2$ | 400 | 68 | 75 |
| Compar. Ex. 4 | W/Al$_2$O$_3$ | 400 | 32 | 33 |
| Compar. Ex. 5 | W/SnO$_2$ | 400 | 41 | 51 |

EXAMPLE 28 AND COMPARATIVE EXAMPLE 6

[Catalyst Reuse Experiment in Hydrogen Peroxide Oxidation of 1-butene]

The catalyst reuse experiment in hydrogen peroxide oxidation of 1-butene was carried out under the following conditions using the catalysts obtained in Preparation Method 6. The catalyst was recovered with filtration. The results are shown in Table 5.

| 1-butene: | bubbling for 10 minutes |
|---|---|
| Aqueous hydrogen peroxide: | 1 mmol |
| Benzonitrile: | 6 mL |
| Reaction temperature: | 60° C. |
| Reaction time: | 2 hours |

Catalyst: 100 μmol of same catalyst was recovered with filtration and used repeatedly.

TABLE 5

| Catalyst | | Number of reaction runs | $H_2O_2$-based yield (%) | Tungsten leaching (%) | Relative rate of leaching (%) |
|---|---|---|---|---|---|
| Example 28 | W/Zn—SnO$_2$ | 1 | 63 | 0 | 0 |
| | | 2 | 67 | 0 | 0 |

TABLE 5-continued

| Catalyst | | Number of reaction runs | H$_2$O$_2$-based yield (%) | Tungsten leaching (%) | Relative rate of leaching (%) |
|---|---|---|---|---|---|
| | | 3 | 64 | 0 | 0 |
| | | 4 | 66 | 0 | 0 |
| | | 5 | 63 | 0 | 0 |
| Compar. Ex. 6 | W/SnO$_2$ | 1 | 43 | 0.09 | — |
| | | 2 | 45 | 0.13 | — |
| | | 3 | 39 | 0.06 | — |
| | | 4 | 33 | 0.10 | — |

EXAMPLES 29 TO 30 AND COMPARATIVE EXAMPLE 7

[Baeyer-Villiger Oxidation Reaction]

The hydrogen peroxide oxidation of cyclohexanone and cyclobutanone was carried out under the following conditions using the catalysts obtained in Preparation Method 6. The results are shown in Table 6.

| | |
|---|---|
| Substrate (cyclohexanone, cyclobutanone): | 1 mmol |
| 60% aqueous hydrogen peroxide: | 1 mmol |
| Benzonitrile: | 2 mL |
| Reaction time: | 18 hours |
| Reaction temperature: | 70° C. |
| Catalyst: | 350 mg |

TABLE 6

| | Catalyst | Substrate | Lactone yield (%) | Tungsten leaching (%) | Relative rate of leaching (%) |
|---|---|---|---|---|---|
| Example 29 | W/Zn—SnO$_2$ | Cyclohexanone | 11 | 0 | 0 |
| Example 30 | W/Zn—SnO$_2$ | Cyclobutanone | 85 | 0 | 0 |
| Compar. Ex. 7 | W/SnO$_2$ | Cyclohexanone | 4.3 | 0.11 | — |

EXAMPLES 31 TO 32 AND COMPARATIVE EXAMPLE 8

[Oxygen Oxidation Reaction of Cyclooctene]

The oxygen oxidation of cyclooctene was carried out under the following conditions using the catalysts obtained in Preparation Method 8. The results are shown in Table 7.

| | |
|---|---|
| Cyclooctene: | 1 mmol |
| Oxygen: | 1 atm |
| Isobutylaldehyde: | 4 mmol |
| Benzonitrile: | 2 mL |
| Reaction time: | 24 hours |
| Reaction temperature: | 100° C. |
| Catalyst: | 350 mg |

TABLE 7

| | Catalyst | Cyclooctene oxide yield (%) | Tungsten leaching (%) | Relative rate of leaching (%) |
|---|---|---|---|---|
| Example 31 | γ-Fe$_2$SiW$_{10}$O$_{38}$/Zn—SnO$_2$ | 13 | 0 | 0 |
| Compar. Example 8 | γ-Fe$_2$SiW$_{10}$O$_{38}$/SnO$_2$ | 8 | 0 | 0 |
| Compar. Ex. 9 | W/SnO$_2$ | 5 | 0.05 | — |

In Tables 1 to 3 and 5 to 7, the term "leaching" means the amount of leaching (mole percent) of the tungsten element leached into the reaction mixture relative to 100 mole percent of the tungsten element supported on the catalyst. The amount of tungsten contained in the catalyst prepared can be determined by fluorescent X ray analysis. In Tables 1 to 3 and 5 to 7, the term "relative rate of leaching (%)" means the tungsten species leaching (mole percent) from the third element-containing catalyst with the tungsten species leaching from the third element-free catalyst being taken as 100 mole percent. In Table 5, the number of reaction runs means the number of repetitions of the reaction in which the same catalyst as recovered by filtration was used. In Tables 1 to 3, the yield means the mole percent of the glycidol formed with the moles of H$_2$O$_2$ fed to the reaction system being taken as a basis (100 mole percent), namely [(moles of product glycidol/moles of H$_2$O$_2$)×100]. The selectivity means the mole percent of the glycidol or acrolein formed with the moles of all the oxidation reaction products being taken as a basis (100 mole percent), namely [(moles of glycidol or acrolein formed/moles of all oxidation reaction products)×100]. In Tables 4 and 5, the yield means the moles of the epoxy compound formed with the moles of H$_2$O$_2$ fed to the reaction system being taken as a basis (100 mole percent), namely [(moles of epoxidation reaction product)/moles of H$_2$O$_2$]×100]. The efficiency of H$_2$O$_2$ utilization is the mole percent of the oxidation reaction products formed with the moles of H$_2$O$_2$ consumed in the reaction being taken as a basis (100 mole percent), namely

[(moles of oxidation reaction products/moles of $H_2O_2$ consumed)×100], where the moles of $H_2O_2$ consumed is [(the moles of $H_2O_2$ fed to the reaction system)−(moles of residual $H_2O_2$)]. The moles of residual $H_2O_2$ can be determined by potentiometric titration using 0.1 M tetraammonium cerium sulfate. In Table 6, the yield means the mole percent of the lactone compound formed with the moles of $H_2O_2$ fed to the reaction system being taken as a basis (100 mole percent), namely [(moles of lactone compound formed/moles of $H_2O_2$)×100]. In Table 7, the yield means the mole percent of the epoxidation reaction product formed with the moles of the substrate fed to the reaction system being taken as a basis (100 mole percent), namely [(moles of epoxidation reaction product/moles of substrate)×100].

As seen from Tables 1 to 3, the leaching of the catalyst component (tungsten species) from the catalysts supporting an additional element(s) other than the tungsten species was suppressed as compared with the catalysts constituted of the inorganic oxide and tungsten species alone.

As seen from Tables 4 and 5, the yields of the oxidation products were higher with the catalysts supporting an additional element(s) other than the tungsten species as compared with the catalysts constituted of the inorganic oxide and tungsten species alone; the former catalysts thus showed improved catalytic activity performance and, in addition, could be recovered and reused with their activity retained. Further, the leaching of the catalyst component (tungsten species) was prevented. As seen from Tables 6 and 7, the yields of the oxidation products were higher with the catalysts supporting an additional element other than the tungsten species as compared with the catalysts constituted of the inorganic oxide and tungsten species alone; the former catalysts thus showed improved catalytic activity performance and, in addition, the leaching of the catalyst component (tungsten species) therefrom was prevented.

The invention claimed is:

1. A method of reducing a tungsten species leaching which is carried out by liquid-phase oxidation reaction using a tungsten species, wherein that, in carrying out said method of liquid-phase oxidation reaction using a catalyst comprising a tungsten species as an essential component, wherein said catalyst is obtained by causing said tungsten species to be supported on a porous support and, further separately causing a third element other than the component elements of said porous support and the tungsten element to be present in said catalyst as a component different from said tungsten species or the porous support; wherein said third element comprises at least one element selected from the group consisting of the elements of the groups 2, 3, 4, 5, 7, 8, 9, 10, 11, 12, 13, 14, 15, 16 and 17 of the periodic table, and wherein a reactant substrate is selected from the group consisting of cyclohexanone, cyclobutanone, unsaturated hydrocarbons having 2 to 15 carbon atoms, a compound having at least one ethylenic double bond and a group selected from —COOH, —CN, —COOR and —OR, wherein R being an alkyl, cycloalkyl, aryl or allylalkyl substituent; or an aryl, allylalkyl, halogen, nitro, sulfo, carbonyl, hydroxyl or ether group, an oxidizing agent used is selected from molecular oxygen, hydrogen peroxide, cumene hydroperoxide, tert-butyl hydroperoxide, peracetic acid, oxygen-hydrogen mixed gases, dinitrogen monoxide, and iodosylbenzene, a reaction temperature is not lower than room temperature, but not higher than 250° C., and a reaction pressure is not lower than ordinary pressure but not higher than $2\times10^7$ Pa, and wherein the reaction is selected from aldehyde formation from a primary alcohol having 2 to 15 carbon atoms, carboxylic acid formation from an aldehyde having 2 to 15 carbon atoms, and ketone formation from a secondary alcohol having 2 to 15 carbon atoms if the liquid-phase oxidation reaction is hydroxyl group oxidation.

2. The method of reducing a tungsten species leaching according to claim 1, wherein said catalyst is a catalyst calcined at a temperature of 300 to 700° C.

3. The method of reducing a tungsten species leaching according to claim 1, wherein said third element comprises at least one element selected from the group consisting of Mg, Ca, La, Re, Fe, Zn, Al, In, Sn, Pb, Sb, Bi and F.

4. The method of reducing a tungsten species leaching according to claim 1, wherein said porous support comprises alumina and/or tin oxide as an essential component(s) and said third element comprises at least one element selected from the group consisting of La, Zn, Al, Sn and Pb and wherein said method of liquid-phase oxidation reaction is a method of liquid-phase epoxidation reaction.

5. The method of reducing a tungsten species leaching according to claim 1, wherein said method of liquid-phase oxidation reaction uses hydrogen peroxide as an oxidizing agent.

6. The method of reducing a tungsten species leaching according to claim 1, wherein said method of liquid-phase oxidation reaction is carried out by oxidation reaction of compound having at least one ethylenic double bond.

7. The method of reducing a tungsten species leaching according to claim 1, wherein said tungsten species content in the catalyst is not less than 1 part by weight but not more than 40 part by weight per 100 parts by weight of a porous support.

8. The method of reducing a tungsten species leaching according to claim 1, wherein said catalyst comprising a tungsten species as an essential component is used for supporting tungstic acid and salts thereof, and salts of heteropolyoxometallate anions comprising tungsten atom, wherein the heteropolyoxometallate anions having tungsten atom are represented by the formula (1):

$$[XW_nO_m]^{q-} \quad (1)$$

wherein X represents a silicon atom or phosphorus atom; (n,m) are (12,40) when there is no deficiency, (11, 39) when there is one deficient structure site, (10, 36) when there are two deficient structure sites, or (9, 34) when there are three deficient structure sites, and q is a positive integer, the value of q being determined by the valence of the element X.

9. The method of reducing a tungsten species leaching according to claim 1, wherein said tungsten species leaching is not more than 99 mole percent when a tungsten species leaching from the third element-free catalyst is taken as 100 mole percent.

10. The method of liquid phase oxidation reaction using a tungsten species according to claim 1,
wherein the substrate is selected from the group consisting of cyclohexanone, cyclobutanone, straight chain alkenes having a terminal ethylenic double bond containing 2 to 15 carbon atoms, alkenes or branched alkenes having an ethylenic double bond in the molecule having 2 to 15 carbon atoms, alicyclic olefinic hydrocarbons having 2 to 15 carbon atoms, allyl alcohol, allyl chloride, allyl methyl ether, allyl vinyl ether, diallyl ether, allyl phenyl ether, methyl methacrylate, and acrylic acid.

* * * * *